(12) United States Patent
Ahearn

(10) Patent No.: US 10,973,477 B2
(45) Date of Patent: Apr. 13, 2021

(54) PORTABLE X-RAY

(71) Applicant: David J. Ahearn, Little Compton, RI (US)

(72) Inventor: David J. Ahearn, Little Compton, RI (US)

( * ) Notice: Subject to any disclaimer, the term of this patent is extended or adjusted under 35 U.S.C. 154(b) by 0 days.

(21) Appl. No.: 16/234,077

(22) Filed: Dec. 27, 2018

(65) Prior Publication Data
US 2019/0200944 A1 Jul. 4, 2019

Related U.S. Application Data

(60) Provisional application No. 62/613,288, filed on Jan. 3, 2018.

(51) Int. Cl.
*F16M 13/00* (2006.01)
*A61B 6/00* (2006.01)

(52) U.S. Cl.
CPC .......... *A61B 6/4405* (2013.01); *A61B 6/4411* (2013.01); *A61B 6/4435* (2013.01); *A61B 6/4452* (2013.01)

(58) Field of Classification Search
CPC ....... F16M 11/05; F16M 11/041; A61G 15/10
See application file for complete search history.

(56) References Cited

U.S. PATENT DOCUMENTS

| | | | |
|---|---|---|---|
| 8,205,847 B2* | 6/2012 | Dorris | F16M 11/041 248/222.52 |
| 8,366,060 B2* | 2/2013 | Hung | F16M 11/041 248/124.1 |
| 9,256,911 B1* | 2/2016 | Parsons | A61G 15/10 |
| 9,706,843 B2* | 7/2017 | Hung | F16M 11/105 |
| 9,752,723 B2* | 9/2017 | Hung | F16M 13/02 |
| 2010/0123061 A1* | 5/2010 | Vlies | F16M 11/2014 248/220.1 |
| 2016/0033426 A1* | 2/2016 | Georgeson | G01N 23/203 378/87 |

* cited by examiner

*Primary Examiner* — Amy J. Sterling
(74) *Attorney, Agent, or Firm* — Adler Pollock & Sheehan P.C

(57) ABSTRACT

A system includes a multi-sectional articulating arm including a first section pivotally secured to a second section, the second section pivotally secured to a third section, a wall mount secured to the first section opposite the second section, and a mounting bracket secured to an end of the third section opposite the second section.

7 Claims, 3 Drawing Sheets

1000

Secure a wall mount to a fixed structure
1010

Secure a pivoting first section of an articulating arm to the wall mount
1020

Secure a pivoting second section of the articulating arm to the pivoting first section
1030

Secure a pivoting third section of the articulating arm to the pivoting second section
1040

Secure a pivoting mounting bracket having a rail mount
1050

Attach a mounting insert bracket of an x-ray camera to the rail mount
1060

FIG. 4

PORTABLE X-RAY

CROSS REFERENCE TO RELATED APPLICATIONS

This application claims benefit from U.S. Provisional Patent Application Ser. No. 62/613,288, filed Jan. 3, 2018, which is incorporated by reference in its entirety.

BACKGROUND OF THE INVENTION

The present invention relates generally to medical X-ray positioners, and more specifically to a portable X-ray.

Conventional X-ray positioners provide mechanical supports to hold an X-ray source and X-ray detector in opposition about a patient for a limited number of specific procedures. For procedures in which the patient is standing, the X-ray source may be attached to a pillar allowing adjustment in its height as directed toward an X-ray detector attached to an opposing wall or a second similar pillar. For procedures in which the patient is supine, the X-ray source and detector may be attached to opposite sides of a patient table. Alternatively the X-ray source and the detector may be attached to opposite ends of a C-arm which is supported by a sliding collar allowing the angle of the X-rays through the patient to be varied.

Such systems require complex multi-axis movement for simple adjustments of the X-ray tube and detector in angulation or translation, and appear to have limited utility for certain common X-ray procedures.

SUMMARY OF THE INVENTION

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In general, in one aspect, the invention features a system including a multi-sectional articulating arm including a first section pivotally secured to a second section, the second section pivotally secured to a third section, a wall mount secured to the first section opposite the second section, and a mounting bracket secured to an end of the third section opposite the second section.

In another aspect, the invention features an articulating arm including a number of sections, a wall mount secured to a first section, and a mounting bracket secured to an end of a third section.

In still another aspect, the invention features a method including securing a wall mount to a fixed structure, pivotally securing a first section of an articulating arm to the wall mount, pivotally securing a second section of the articulating arm to the first section of the articulating arm, pivotally securing a third section of the articulating arm to the second section of the articulating arm, and pivotally securing a mounting bracket to the third section.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

These and other features, aspects, and advantages of the present invention will become better understood with reference to the following description, appended claims, and accompanying drawings where:

FIG. 4 is a flow diagram.

DETAILED DESCRIPTION

Figure 1:
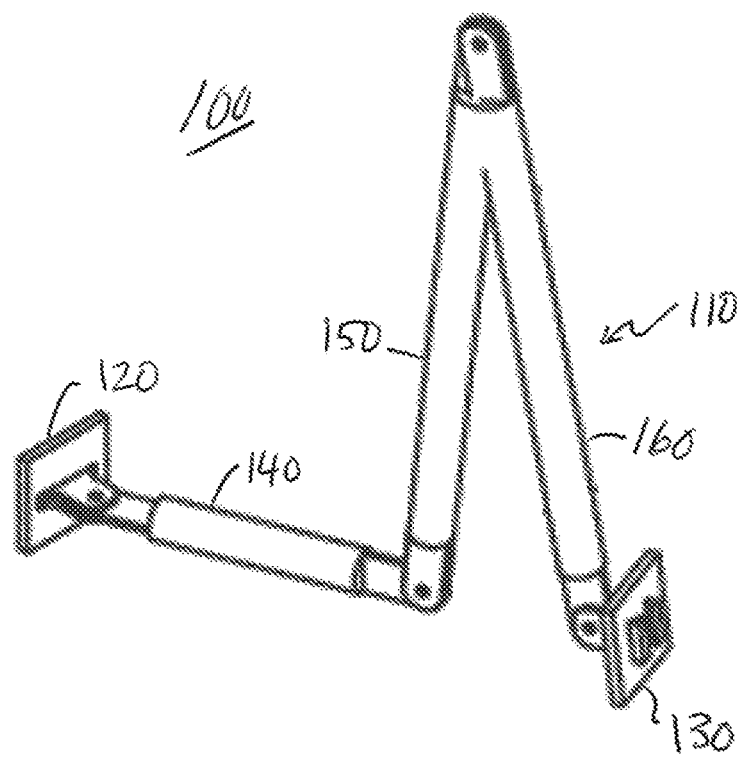
FIG. 1 is block diagram.

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

The present invention provides a simplified mechanism for independently supporting an X-ray camera for greater positioning flexibility yet providing simplified axis motion for typical repositioning actions.

As shown in FIG. 1, an exemplary portable X-ray 100 includes an articulating arm 110. The articulating arm 110 includes a wall mount 120 at one terminus and a mounting bracket 130 at an opposite terminus. The articulating arm 110 includes three main sections 140, 150, 160. Section 140 is pivotally secured to the wall mount 120. Section 140 is further pivotally secured to section 150 and section 150 is pivotally secured to section 160. The mounting bracket 130 is pivotally secured to the section 160. Although the articulating arm 110 is shown to include three main sections 140, 150, 160, fewer or greater number of sections may be provided.

The wall mount 120 is configured to securely attach section 140 of the articulating arm 110 to a structure such as a wall using, for example, nails, screws, adhesive or other such attachment aids or fixation devices.

Figure 2:
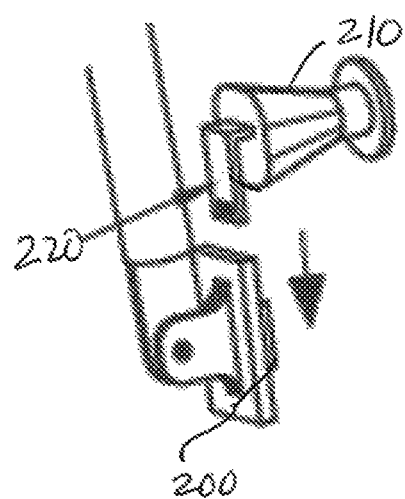
FIG. 2 is a block diagram.

As shown in FIG. 2, the mounting bracket 130 includes a rail mount 200. The rail mount 200 is configured to receive an external device, such as a swappable X-ray camera 210 fitted with an X-ray mounting insert bracket 220. The X-ray mounting insert bracket 220 enables mounting and dismounting of the swappable X-ray camera 210 to and from the rail mount 200. More specifically, the X-ray mounting insert bracket 220 is adapted to be removably secured to the rail mount 200.

Figure 3:
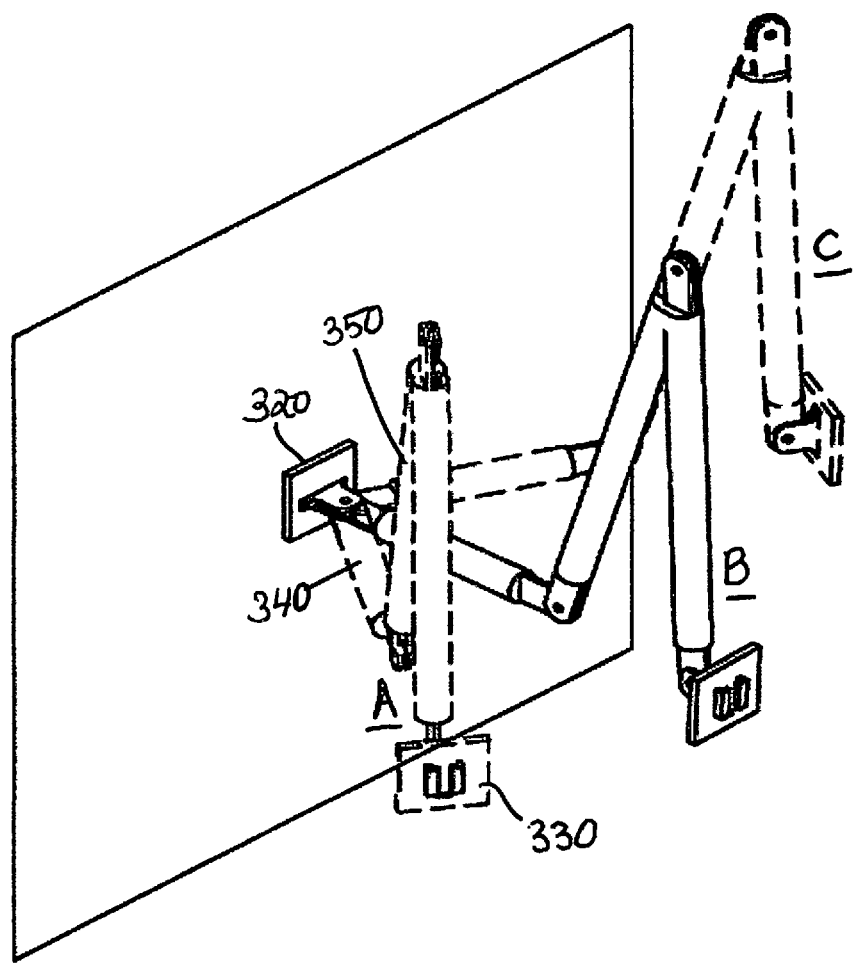
FIG. 3 is a block diagram.

As shown in FIG. 3, the portable X-ray 300 is configured to enable maximum flexibility of movement in three dimensions. Three exemplary positions A, B, C are illustrated. More specifically, a link from the wall mount 320 to section 340, the link from section 340 to section 350, and the link from section 360 to the mounting bracket 330, enable movement of the swappable X-ray camera 210 (of FIG. 2) in any of three dimensions. Each of the sections 330, 340, 350 be may independently articulated, each having at least two independent axes of motion.

As shown in FIG. 4, a process 1000 includes securing (1010) a wall mount to a fixed structure.

Process 1000 secures (1020) a pivoting first section of an articulating arm to the wall mount.

Process 1000 secures (1030) a pivoting second section of the articulating arm to the pivoting first section.

Process 1000 secures (1040) a pivoting third section of the articulating arm to the pivoting second section.

Process 1000 secures (1050) a pivoting mounting bracket having a rail mount.

Process 1000 attached (1050) a mounting insert bracket of an X-ray camera to the rail mount.

It would be appreciated by those skilled in the art that various changes and modifications can be made to the illustrated embodiments without departing from the spirit of the present invention. All such modifications and changes are intended to be within the scope of the present invention except as limited by the scope of the appended claims.

What is claimed is:

1. A system comprising:
   a multi-sectional articulating arm comprising a first section pivotally secured to a second section, the second section pivotally secured to a third section;
   a wall mount secured to the first section opposite the second section;
   a mounting bracket pivotally secured to an end of the third section opposite the second section, the mounting bracket comprising a rail mount comprising two spaced elongated parallel members that both project outwardly from an outer surface of a base that is pivotally coupled to the end of the third section of the articulating arm that is opposite the second section of the articulating arm, and wherein the outer surface of the base extends between the elongated parallel members;
   a mounting insert bracket affixed to a swappable X-ray camera and comprising a tab fixed to and spaced from the x-ray camera and configured to slide onto the outer surface of the base between the parallel members; and
   the mounting bracket enabling mounting and dismounting of the mounting insert bracket affixed to the swappable X-ray camera to and from the two spaced parallel members of the rail mount of the mounting bracket secured to the end of the third section, thus enabling mounting and dismounting of the swappable X-ray camera.

2. The system of claim 1 further comprising a wall, the wall mount of the first section secured to the wall.

3. An articulating arm comprising:
   a plurality of sections;
   a wall mount secured to a first section; and
   a mounting bracket pivotally secured to an end of a third section, the mounting bracket comprising a rail mount comprising two spaced elongated parallel members that both project outwardly from an outer surface of a base that is pivotally coupled to the end of the third section of the articulating arm that is opposite the second section of the articulating arm, and wherein the outer surface of the base extends between the elongated parallel members;
   a mounting insert bracket affixed to a removable device and comprising a tab fixed to and spaced from the removable device and configured to slide onto the outer surface of the base between the parallel members; and
   the mounting bracket enabling mounting and dismounting of the mounting insert bracket affixed to the removable device to and from the two spaced parallel members of the rail mount of the mounting bracket secured to the end of the third section, thus enabling mounting and dismounting of the removable device.

4. The articulating arm of claim 3 further comprising a second section, a first end of the second section pivotally attached to an and of the first section opposite the wall mount, an opposite end of the second section pivotally attached to an end of the third section opposite the mounting bracket.

5. The articulating arm of claim 4 wherein the wall mount is configure to be secured to a fixed structure.

6. The articulating arm of claim 5 wherein the removable device is a swappable X-ray camera.

7. A method comprising:
   securing a wall mount to a fixed structure;
   pivotally securing a first section of an articulating arm to the wall mount;
   pivotally securing a second section of the articulating arm to the first section of the articulating arm;
   pivotally securing a third section of the articulating arm to the second section of the articulating arm;
   pivotally securing a mounting bracket to the third section, the mounting bracket comprising a rail mount comprising two spaced elongated parallel members that both project outwardly from an outer surface of a base that is pivotally coupled to the end of the third section of the articulating arm that is opposite the second section of the articulating arm, and wherein the outer surface of the base extends between the elongated parallel members, and wherein the elongated parallel members are configured to receive from above a mounting insert bracket affixed to a swappable X-ray camera, wherein the mounting insert bracket comprises a tab fixed to and spaced from the x-ray camera and configured to slide onto the outer surface of the base between the parallel members; and
   mounting and dismounting the mounting insert bracket affixed to the swappable X-ray camera to and from the two spaced parallel members of the rail mount of the mounting bracket secured to the end of the third section.

* * * * *